United States Patent [19]

Meola née Vannini

[11] Patent Number: 4,774,936
[45] Date of Patent: Oct. 4, 1988

[54] STABILIZING PROSTHESIS DEVICE PARTICULARLY FOR USE BY PARAPLEGIC PATIENTS

[76] Inventor: Antonietta M. Meola née Vannini, Via S. Stefano 130, Bologna, Italy

[21] Appl. No.: 38,484

[22] Filed: Apr. 13, 1987

Related U.S. Application Data

[63] Continuation of Ser. No. 820,766, Jan. 21, 1986, abandoned.

[30] Foreign Application Priority Data

Jan. 23, 1985 [IT] Italy ................................ 3312 A/85

[51] Int. Cl.$^4$ .............................................. A61F 5/00
[52] U.S. Cl. .................................................. 128/80 R
[58] Field of Search .................. 128/89 R, 83.5, 87 R,
128/80 R, 80 A, 80 B, 80 C, 80 D, 80 DB, 80 E,
80 F, 80 G, 80 H, 80 J; 36/88, 89, 93

[56] References Cited

U.S. PATENT DOCUMENTS

| | | | |
|---|---|---|---|
| 1,692,896 | 11/1928 | Hilgert | 36/89 |
| 3,814,088 | 6/1974 | Raymond | 128/80 H |
| 4,057,056 | 11/1977 | Payton | 128/83.5 |
| 4,217,893 | 8/1980 | Payton | 128/89 R |
| 4,446,856 | 5/1984 | Jordan | 128/83.5 |
| 4,505,269 | 3/1985 | Davies et al. | 128/87 R |

Primary Examiner—Ronald L. Frinks
Assistant Examiner—James Prizant
Attorney, Agent, or Firm—Laff, Whitesel, Conte & Saret

[57] ABSTRACT

The stabilizing prosthesis device comprises a functional skeletal structure having a rigid flat sole extending parallel to the ground surface, and at least one upright half-shell adapted to at least partially envelop the patients's limb and provided with means of anchoring the limb. Extending between the sole and the half-shell there being a connection part having a bottom portion defining a sloping upper surface whereby the patient's center of gravity can be shifted forward in alignment with the extension of the sole.

6 Claims, 2 Drawing Sheets

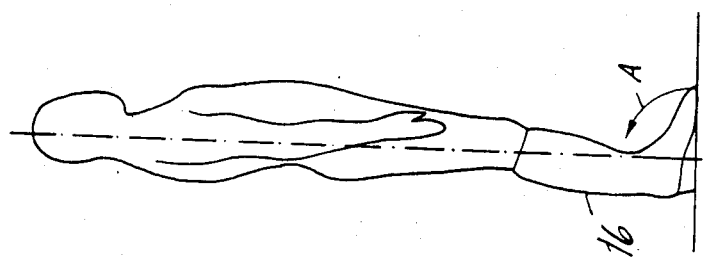
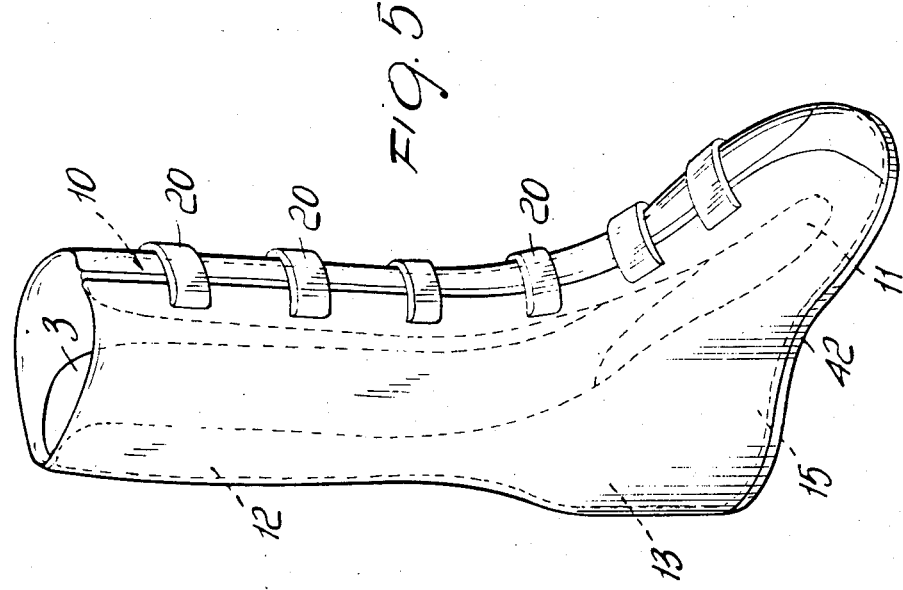

STABILIZING PROSTHESIS DEVICE PARTICULARLY FOR USE BY PARAPLEGIC PATIENTS

This is a continuation of application Ser. No. 06/820,766 filed Jan. 21, 1986, now abandoned.

BACKGROUND OF THE INVENTION

The subject of this invention is a stabilizing prosthesis device or stabilizing brace particularly for use by paraplegic patients.

As is known, people afflicted by varying degrees of paralysis of the lower limbs have been forced heretofore to make continuous use of wheelchairs in order to enjoy a measure of mobility and independence. Still nowadays, the upright stance can only be ensured for paraplegic patients through the application of static apparatus to which they are bound, or alternatively through large-size apparatus such as, for example, caliper splints, which encircle the lower limbs and the pelvis, thereby blocking articulation of the ankle, knee and hip joints in order to prevent the patient's lower limbs from collapsing under gravity.

It is only by the application of such large-size apparatus, and following extended training, that a limited number of paraplegic patients succeed to make just a few steps with their lower limbs held stretched rigidly in the apparatus itself. They are forced, anyhow, to stand on the lower limbs by leaning on walking sticks or crutches.

The few steps that such patients occasionally succeed to make require cnsiderable effort on their part, and do not in fact represent any improvement in the patient's independence because the patient can not attend to any activities either just standing up or whilst walking, because all of his/her concentration and physical effort is required to merely maintain his/her rather uncertain balance.

To pursue his/her habitual tasks, the patient is forced, therefore, to make continuous use of a wheelchair, in which the patient has his/her upper limbs available for ordinary and occupational bodily movements.

Thus, a patient such as a paraplegic patient, afflicted with at least partial paralysis of the lower limbs is afforded as yet neither orthopedic instruments which can permit him/her to assume a safe upright stance in which to simultaneously attend to other manual activities, nor orthopedic instruments enabling a physiological gait for a minimum expenditure of energy whilst being aesthetically acceptable.

SUMMARY OF THE INVENTION

It is the technical aim of this invention to solve the above-outlined problems by providing a stabilizing brace which affords, particularly for the paraplegic patient afflicted with total or partial paralysis of the lower limbs the possibility of assuming, upon training, a comfortable and safe upright stance even without leaning on canes, as well, eventually, as an efficient and independent deambulation using his/her own lower limbs.

Within the above aim, it is a further object of the invention to provide a stabilizing brace which is of simple design, easy to use, and which can be readily put on and removed like ordinary footwear, while being satisfactory also from an aesthethic standpoint.

The above aim and object are achieved, according to the invention, by this stabilizing brace particularly for use by paraplegic patients, which is characterized in that it comprises a functional skeletal structure including a substantially flat sole of rigid construction, adapted for resting on the ground surface, and extending substantially parallel thereto, at least one upright shell portion adapted to at least partially enclose the patient's lower limb and being provided with securing means for anchoring said brace to said patient's lower limb, and a connecting part extending between said flat sole and said half-shell, said connecting part having a bottom portion defining an upper surface set at an inclination angle effective, in use, to shift the patient's center of gravity forward in alignment with said extension of said sole adapted for resting on the ground.

BRIEF DESCRIPTION OF THE DRAWINGS

The invention details will be more clearly understood from the following description of a preferred embodiment of this stabilizing prosthesis device or stabilizing brace with reference to the accompanying illustrative drawing, where:

FIG. 4 is a diagram illustrating the utilization of the stabilizing brace according to the invention; and FIG. 5 is a perspective view of the inventive stabilizing brace as completed with a covering and provided with fastening straps.

DESCRIPTION OF THE PREFERRED EMBODIMENTS

Figure 1:
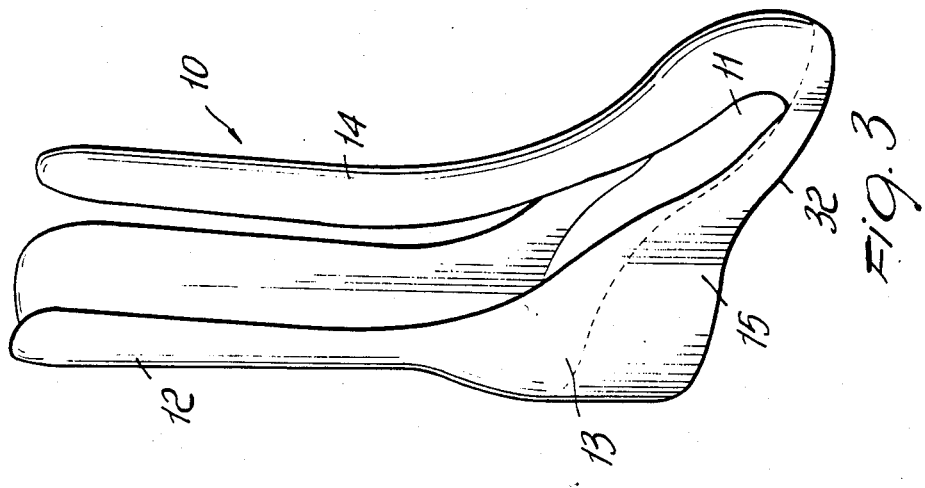
FIG. 1 is a perspective view of the functional skeletal structure of a stabilizing brace particularly for paraplegic patients afflicted by total paralysis of the lower limbs.

With reference first to FIG. 1, the functional skeletal structure of a stabilizing brace generally designated with the reference numeral 1, is especially configured, particularly for use by paraplegic patients afflicted with total paralysis of the lower limbs.

This skeletal structure comprises essentially a substantially flat sole or outsole 2, which is rigid, and extends parallel to the ground surface; a rear upright half-shell or shell portion 3, also rigid and adapted to at least partially enclose the leg; and a connecting part 4 extending between said flat sole 2 and said half-shell 3, being highly rigid and variously angled to fit the morphology of the foot and the tibial-tarsal.

The connecting part 4 comprises a bottom or lower portion 5 which is formed in a cuneform or wedge-like fashion with anterior-posterior and lateral-lateral or camber inclines defining differing thickness dimensions and inclincation angles, so as to provide an upper surface defining an insole 2a which is effective to bring the patient's center of gravity over the axis of the foot's front area of rest onto the ground.

The skeletal structure 1 is advantageously formed from such rigid materials as metal alloys, resins, and the like. Expediently, the correct insole inclination angles and thickness dimensions required for each patient may be determined by techniques such as, for example, making a plaster mould, of the patients lower limb and foot wherefrom the exact required brace conformation can be measured.

Thereafter, the thus formed skeletal structure may be variously coated to provide a shoe of varying shape and design to meet the patient's aesthetic requirements.

In particular, a lightweight or open version is conveniently envisaged for home use which is equipped with fastening straps at different locations on the leg and foot portions; also a closed version is envisaged of boot-like configurationn (FIG. 5) for outdoor use which is expediently covered with an appropriate material as commonly used in the footwear industry such as leather. In this case the fastening straps are located on the boot's exterior covering and may be variously located according to the patient's aesthetic requirements and the need to securely anchor the brace at the interior of the boot to the patient's leg. Obviously other fastening/anchorage arrangements may be envisaged such as a zip fastener, a laced arrangement or any other suitable fastening means or combination thereof.

The skeletal structure 1 would also advantageously incorporate a suitable inner padding, particularly at the insole 2a, and a still outsole 42 (FIG. 5), preferably formed of rubber or the like "non-slip" material.

Figure 2:
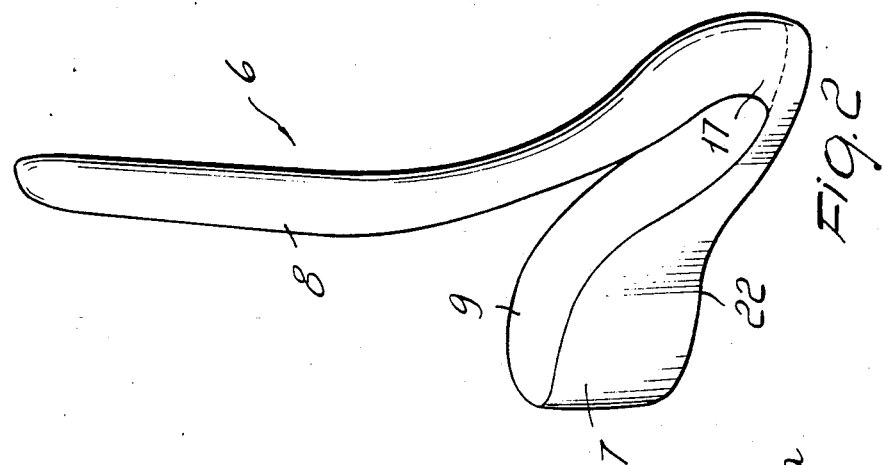
FIG. 2 is a perspective view of the functional skeletal structure of a stabilizing brace particularly for paraplegic patients afflicted by partial paralysis of the lower limbs.

FIG. 2 shows the functional skeletal structure, generally indicated at 6, of a stabilizing prosthesis device or stabilizing brace particularly intended for patients afflicted with partial paralysis of the lower limbs.

That skeletal structure defines essentially a linear sole 22, a rigid bottom 7, a forward tibial half-shell or shell portion 8 of curvilinear conformation which is connected to said bottom 7 at its distal forward portion, and a small connection part 17 extending between the sole 22 and the shell portion 8.

The bottom 7 is similar to that of the skeletal structure 1 and has, in particular, a linear sole 22 which extends substantially flat and parallel to ground and an appropriately inclined insole or upper surface 9.

The tibial half-shell 8 is expediently formed from a material, such as polypropylene, acrylic laminates, steel, and the like, having elastic properties commensurate to the patient's individual requirements.

Also in this case, the skeletal structure is advantageously internally padded or lined, may be variously covered according to aesthetic requirements, and has an outsole 42 of rubber or other suitable material. In particular, the tibial half-shell 8 can be secured to the foot and the leg by means of adjustable straps 20, which may be advantageously located externally on the outer cover 21 as clearly shown in drawing FIG. 5. Thus the brace as worn by the patient substantially resembles an ordinary item of footwear such as a boot.

Figure 3:
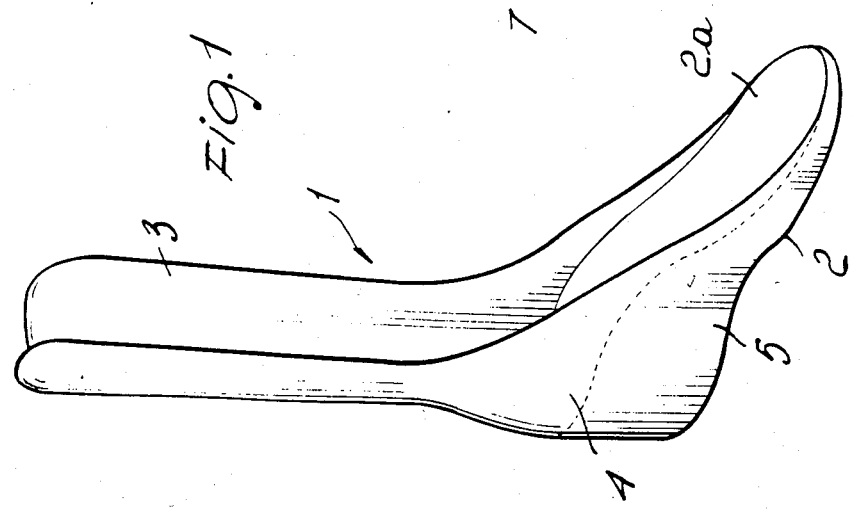
FIG. 3 is a perspective view of the functional skeletal structure of a stabilizing brace particularly for paraplegic patients afflicted by paralysis of an intermediate type.

FIG. 3 shows, lastly, the functional skeletal structure 10 of a brace envisaged for patients afflicted with paralysis of an intermediate type.

That skeletal structure comprises a linear flat sole 32, a rear upright half-shell 12, a connection part 13 extending between said sole 32 and said half-shell 12, an appropriately inclined insole 11 and a forward tibial half-shell 14 connected at the front of the insole 11 with its forward distal portion, the reference numeral 15 denoting the rigid bottom. Thus, the brace consists essentially of a skeletal structure of the same type as that shown in FIG. 1, but having in addition a forward tibial half-shell of the type shown in FIG. 2. That is, it affords combined utilization of the previously described structures, according to contingent requirements and the characteristics of the terrain. For instance, when walking along an uphill path, the limb will urge away from the rear half-shell 12 and rely on the forward half-shell 14, to maintain the patients centre of balance over the ground contact area.

Like in the preceding cases, the skeletal structure is expediently padded or lined, and externally covered to suit the patient's demands.

It has been found in actual practice that the brace disclosed herein, throughout its varying embodiments to suit different degrees of lower limb paralysis, affords a patient the possibility, upon training, to stand up and eventually to walk, thanks in particular to the slight displacement of the patient's center of gravity involved. The mechanism which enables the patient to maintain an upright stance is shown diagrammatically in FIG. 4, where the reference numeral 16 designates a generic brace which causes, in practice, the foot and leg to be blocked in an L-like configuration according to the arrangement of the shell portion with respect to the upper surface of the connecting part. Since the gravitational axis is shifted forward owing to the sloping insole 2a,9,11 an inclined thrust is applied to the brace in the direction A, which combined with the knee constraint effect, enables the patient to stand up, also by taking advantage of his/her balance-keeping ability.

It should be emphasized that in practice, habitual use of the force according to the invention has also been shown to improve trophism of the lower limbs both as concerns their osteo-articular and neuromuscular components. Their use, moreover, by allowing a physiological use of the lower limbs, leads with time to a demonstrated improvement of the inntrinsic motivity of the limbs themselves, by acting as a truly rehabilitative and therapeutic instrument, as well as an aid in training the patient to walk.

Obviously, whilst reference is made herein to the utilization of the stabilizing brace according to the invention by paraplegic patients, it will be appreciated that it may be advantageously utilized by other similarly handicapped patients.

Concurrently therewith, a higher and faster restoration of the patient to normal life can be attained, shortening his/her period of hospitalization or confinement to guarded environments, while affording for the patient upon training, a means of overcoming the architectural barries such as steps, steep inclines, narrow doorways etc. normally present in the environment which, in a known manner, would prevent the patient from gaining access by other means such as a wheelchair.

The invention as disclosed herein may obviously be modified or adapted to suit various contingent requirements, without by doing so, departing from the purview of the instant inventive concept.

Furthermore, any materials may be used providing that they are suitable for the intended application.

I claim:

1. A stabilizing prosthesis brace device particularly for use by paraplegic patients, comprising a functional skeletal structure including a rigid cuneiform sole with a substantially flat bottom surface adapted to rest on a flat surface on which a patient may be standing and extending substantially parallel thereto, at least one upright tibial half-shell portion rigidly attached to the toe of the sole and adapted for at least partially enclosing a patient's lower limb to fix the angle between the foot and leg of the wearer, and said sole having an upper surface extending between a flat heel portion and said toe where said tibial half-shell is attached, said upper surface of said sole having a portion defining an upper surface set at an inclination angle raising toward the heel which is effective, in use, to shift the wearer's center of gravity forward in alignment with said extension of said sole.

2. A stabilizing prosthesis device according to claim 1, comprising a rigid rear upright half-shell adapted to at least partially enclose the patient's leg, said rear upright half-shell being rigidly connected to said sole.

3. A stabilizing prosthesis device according to claim 1, comprising a rigid rear upright shell portion connected to at least the heel portion of said flat sole, and said tibial half-shell is an elastically deformable shell portion connected to said flat sole at its forward distal portion, said shell portions enabling alternate bearing of the patient's limbs according to walking conditions encountered by the patient.

4. A stabilizing prosthesis device according to claim 1, wherein said cuneiform sole defines anterior-posterior and lateral-lateral inclinations with different thickness dimensions and inclination angles to suit the morphology and somatic type of the patient.

5. A stabilizing prosthesis device according to claim 1, wherein said prosthesis includes securing means comprising straps located on the leg and the foot portion of said device.

6. A stabilizing prosthesis device according to claim 1, wherein said functional skeletal structure is coated to fashion a shoe.

* * * * *